United States Patent
Raddatz et al.

[11] Patent Number: 5,310,744
[45] Date of Patent: May 10, 1994

[54] QUINOLYLMETHOXYPHENYL-ACETAMIDES

[75] Inventors: Siegfried Raddatz, Cologne; Klaus-Helmut Mohrs; Michael Matzke, both of Wuppertal; Romanis Fruchtmann, Cologne; Armin Hatzelmann, Constance; Reiner Müller-Peddinghaus, Bergisch Gladbach, all of Fed. Rep. of Germany

[73] Assignee: Bayer Aktiengesellschaft, Leverkusen, Fed. Rep. of Germany

[21] Appl. No.: 979,745

[22] Filed: Nov. 23, 1992

[30] Foreign Application Priority Data

Dec. 3, 1991 [DE] Fed. Rep. of Germany ....... 4139749

[51] Int. Cl.$^5$ .................. C07D 215/14; A61K 31/47; A61K 31/495
[52] U.S. Cl. .................. 514/314; 514/235.2; 514/255; 514/311; 514/312; 544/128; 544/363; 546/153; 546/155; 546/156; 546/157
[58] Field of Search .............. 544/128, 363; 546/153, 546/155, 156, 157, 175; 514/235.2, 311, 312, 314, 255

[56] References Cited

U.S. PATENT DOCUMENTS 4,970,215  11/1990  Mohrs .................................. 514/311

FOREIGN PATENT DOCUMENTS 0344519  12/1989  European Pat. Off. ........... 546/174

OTHER PUBLICATIONS

Chemical Abstracts, vol. 114, No. 17, Abstract No. 164.036q, Apr. 29, 1991 p. 758.
Chemical Abstracts, vol. 113, No. 9, Abstract No. 78.180e, Aug. 27, 1990, p. 763.
Chemical Abstracts, vol. 113, No. 7, Abstract No. 58,959n, Aug. 13, 1990, p. 682.

Primary Examiner—C. Warren Ivy
Assistant Examiner—Zinna N. Davis
Attorney, Agent, or Firm—Sprung Horn Kramer & Woods

[57] ABSTRACT

Quinolylmethoxyphenyl-acetamides of the formula:

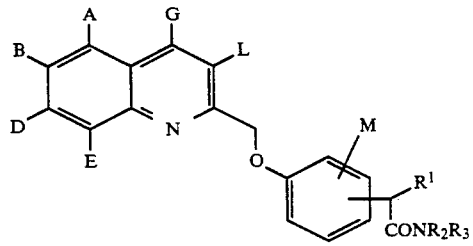

in which

A, B, D, E, G, L and M are hydrogen, hydroxyl, halogen, cyano, carboxyl, nitro, trifluoromethyl, trifluoromethoxy, alkyl, alkoxy or optionally substituted aryl;

$R_1$ represents optionally substituted cycloalkyl; and $R_2$ and $R_3$ independently represent hydrogen, alkyl, benzyl, or optionally substituted cycloalkyl; or together represent piperidinyl, morpholino, or piperazinyl;

show a high in vitro activity as leukotriene synthesis inhibitors and, therefore, are suitable for the treatment and prevention of inflammations.

11 Claims, No Drawings

QUINOLYLMETHOXYPHENYL-ACETAMIDES

The invention relates to quinolylmethoxyphenyl-acetamides, to processes for their preparation and to their use in medicaments.

It is already known that substituted 4-(quinolin-2-yl-methoxy)phenylacetic acid derivatives and substituted (quinolin-2-yl-methoxy)phenyl-acylsulphonamides have a lipoxygenase-inhibiting action (cf. EP 344,519 A and EP 399,291 A).

The present invention relates to quinolylmethoxyphenylacetamides of the general formula (I)

(I)

[Structure: quinoline ring with positions A, B, D, E labeled on benzene ring, G, L on pyridine ring, N as ring nitrogen, connected via CH$_2$-O to phenyl ring with substituent M, bearing *CH(R$_1$)-CO-NR$_2$R$_3$]

in which

A, B, D, E, G, L and M independently of one another represent hydrogen, hydroxyl, halogen, cyano, carboxyl, nitro, trifluoromethyl, trifluoromethoxy or represent straight-chain or branched alkyl or alkoxy each having up to 8 carbon atoms, or represent aryl having 6 to 10 carbon atoms, which is optionally substituted by halogen, hydroxyl, nitro or cyano, $R^1$ represents cycloalkyl having 3 to 12 carbon atoms, which is optionally substituted by straight-chain or branched alkyl having up to 8 carbon atoms, $R^2$ and $R^3$ are identical or different and represent hydrogen or straight-chain or branched alkyl having up to 8 carbon atoms, or represent benzyl, or represent cycloalkyl having 3 to 12 carbon atoms, which is optionally substituted by straight-chain or branched alkyl having up to 8 carbon atoms, or $R^2$ and $R^3$, together with the nitrogen atom, form a heterocyclic ring of the formula $-N\big\langle\underset{\phantom{x}}{\phantom{xx}}\big\rangle$, $-N\big\langle\underset{\phantom{x}}{\phantom{xx}}\big\rangle O$ or $-N\big\langle\underset{\phantom{x}}{\phantom{xx}}\big\rangle N-R_4$ in which $R^4$ denotes straight-chain or branched alkyl or alkenyl each having up to 8 carbon atoms, each of which is optionally substituted by phenyl or denotes phenyl which is optionally substituted by halogen or trifluoromethyl, optionally in an isomeric form, and to their salts.

Surprisingly, the quinolylmethoxyphenyl-acetamides of the general formula (I) according to the invention show a high in vitro activity as leukotriene synthesis inhibitors.

In the context of the present invention, physiologically acceptable salts are preferred. Physiologically acceptable salts of the quinolylmethoxyphenyl-acetamides can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are additionally salts of the univalent metals, such as alkali metals, and the ammonium salts. Sodium, potassium and ammonium salts are preferred.

The compounds according to the invention exist in stereoisomeric forms (*), which either behave as image and mirror image (enantiomers) or which do not behave as image and mirror image (diastereomers). The invention relates both to the antipodes and to the racemic forms as well as the diastereo mixtures. Like the diastereomers, the racemic forms can also be separated in a known manner into the stereoisomerically uniform constituents (cf. E. L. Eliel, Stereochemistry of Carbon Compounds, McGraw Hill, 1962).

Preferred compounds of the general formula (I) are those in which

A, B, D, E, G, L and M independently of one another represent hydrogen, hydroxyl, fluorine, chlorine, bromine, carboxyl, nitro, trifluoromethyl, trifluoromethoxy or represent straight-chain or branched alkyl or alkoxy each having up to 6 carbon atoms, or represent phenyl which is optionally substituted by fluorine, chlorine, bromine, hydroxyl, nitro or cyano, $R^1$ represents cyclopropyl, cyclobutyl, cyclopentyl, cyclohexyl, cycloheptyl or cyclooctyl, each of which is optionally substituted by straight-chain or branched alkyl having up to 6 carbon atoms, $R^2$ and $R^3$ are identical or different and represent hydrogen or straight-chain or branched alkyl having up to 6 carbon atoms, or represent benzyl, or represent cyclopropyl, cyclobutyl, cyclopentyl, cyclohexyl, cycloheptyl or cyclooctyl, each of which is optionally substituted by straight-chain or branched alkyl having up to 6 carbon atoms, or $R^2$ and $R^3$, together with the nitrogen atom, form a heterocyclic ring of the formula $-N\big\langle\underset{\phantom{x}}{\phantom{xx}}\big\rangle$ or $-N\big\langle\underset{\phantom{x}}{\phantom{xx}}\big\rangle N-R_4$ in which $R^4$ denotes straight-chain or branched alkyl or alkenyl each having up to 6 carbon atoms, each of which is optionally substituted by phenyl or denotes phenyl which is optionally substituted by fluorine, chlorine or trifluoromethyl, if appropriate in an isomeric form, and their salts.

Particularly preferred compounds of the general formula (I) are those
in which

A, B, D, E, G, L and M independently of one another represent hydrogen, hydroxyl, fluorine, chlorine, bromine or straight-chain or branched alkyl having up to 4 carbon atoms, $R^1$ represents cyclopropyl, cyclopentyl, cyclohexyl or cycloheptyl, each of which is optionally substituted by straight-chain or branched alkyl having up to 4 carbon atoms, $R^2$ and $R^3$ are identical or different and represent hydrogen or straight-chain or branched alkyl having up to 4 carbon atoms, or represent benzyl, or represent cyclopropyl, cyclopentyl, cyclohexyl or cycloheptyl, each of which is optionally substituted by straight-chain or branched alkyl having up to 4 carbon atoms, or R$^2$ and R$^3$, together with the nitrogen atom, form a heterocyclic ring of the formula

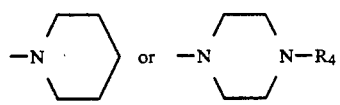

in which

R$^4$ denotes straight-chain or branched alkyl or alkenyl each having up to 4 carbon atoms, each of which is optionally substituted by phenyl or denotes phenyl which is optionally substituted by fluorine, chlorine or triffluoromethyl, optionally in an isomeric form, and their salts.

Very particularly preferred compounds of the general formula (I) are those
in which
A, B, D, E, G and L represent hydrogen or chlorine.

Those compounds are also very particularly preferred in which the radical

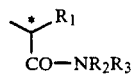

is in the 4-position to the quinolylmethoxy radical.

Processes for the preparation of the compounds of the general formula (I) according to the invention have additionally been found, characterized in that

[A] acids of the general formula (II)

in which

A, B, D, E, G, L, M and R$^1$ have the abovementioned meaning, after activation of the carboxylic acid function, for example via the acid halides, anhydrides or imidazolides, in organic solvents, are amidated with amines of the general formula (III)

$$HNR^{2'}R^{3'} \quad (III)$$

in which

R$^{2'}$ and R$^{3'}$ have the abovementioned meaning of R$^2$ and R$^3$, but do not simultaneously represent hydrogen, in inert solvents, if appropriate in the presence of a base, or reacted with ammonia/ammonium chloride, or

[B] cyano compounds of the general formula (IV)

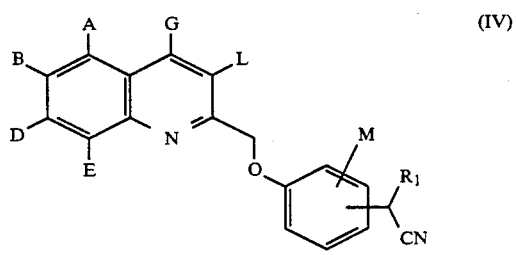

in which

A, B, D, E, G, L, M and R$^1$ have the abovementioned meaning, are reacted with acids, preferably hydrochloric acid, and if R$^2$ and/or R$^3$ do not denote hydrogen, an alkylation of the amino group optionally also follows, and the substituents A, B, D, E, G, L and M are optionally varied according to customary methods.

The process according to the invention can be illustrated by way of example by the following reaction scheme:

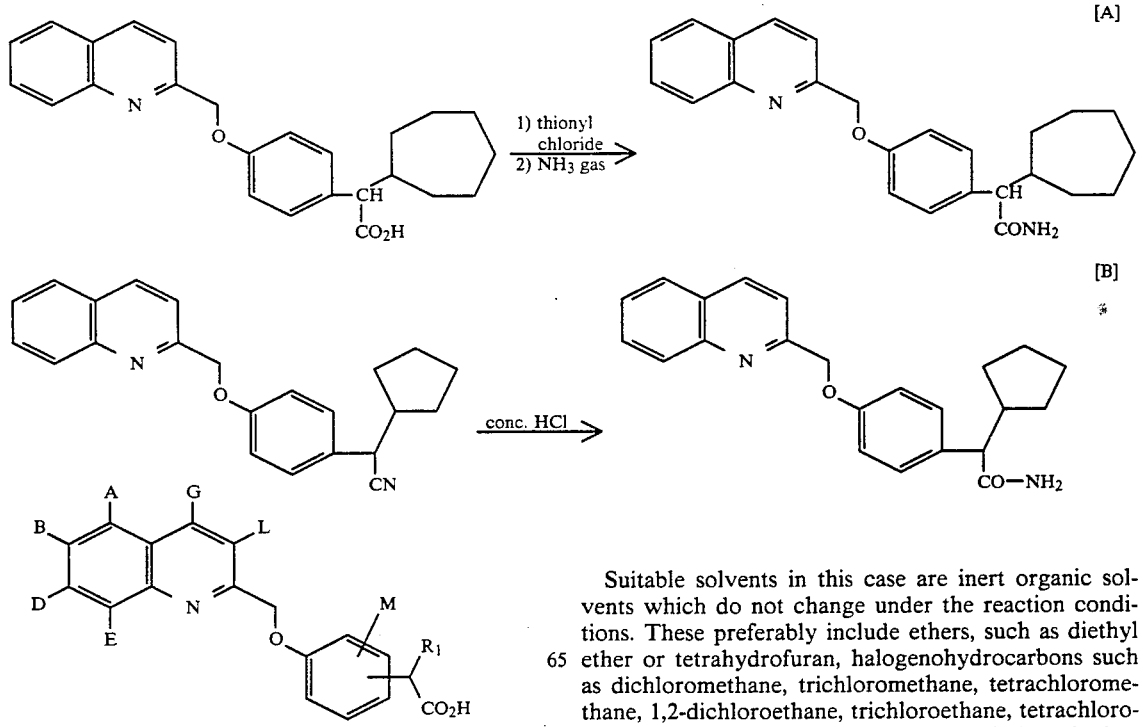

Suitable solvents in this case are inert organic solvents which do not change under the reaction conditions. These preferably include ethers, such as diethyl ether or tetrahydrofuran, halogenohydrocarbons such as dichloromethane, trichloromethane, tetrachloromethane, 1,2-dichloroethane, trichloroethane, tetrachloroethane, 1,2-dichloroethane or trichloroethylene, hydrocarbons such as benzene, xylene, toluene, hexane, cyclohexane or mineral oil fractions, nitromethane, dimethylformamide, acetone, acetonitrile or hexamethylphosphoramide. It is also possible to employ mixtures of these solvents. Dichloromethane, tetrahydrofuran, acetone and dimethylformamide are preferred.

Suitable bases for the individual process steps, in particular for the amidation, are the customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate, potassium carbonate, or alkali metal alkoxides such as, for example, sodium methoxide or ethoxide, potassium methoxide or ethoxide or potassium tert-butoxide, or organic amines such as benzyltrimethylammonium hydroxide, tetrabutylammonium hydroxide, pyridine, triethylamine, piperidine or N-methylpiperidine. Potassium carbonate, sodium hydride, sodium hydrogencarbonate and piperidine are preferred.

The amidation is in general carried out in a temperature range from 0° C. to 150° C., preferably at 25° C. to 40° C.

The amidation is in general carried out at normal pressure. However, it is also possible to carry out the process at reduced pressure or at elevated pressure (for example in a range from 0.5 to 5 bar).

In particular if $R^2$ and $R^3$ have the meaning of hydrogen, it has proved expedient to carry out the reaction in a stream of ammonia, under certain circumstances with slightly elevated pressure.

Suitable reagents for activating the carboxylic acid are the customary ones such as inorganic halides, for example thionyl chloride, mesyl chloride, phosphorus trichloride or phosphorus pentachloride, or carbonyldiimidazole, carbodiimides such as cyclohexyl carbodiimide or 1-cyclohexyl-3-[2-(N-methylmorpholino)ethyl]-carbodiimide p-toluenesulphonate or N-hydroxylphthalimide or N-hydroxy-benzotriazole.

Suitable solvents for the alkylation are likewise customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane is preferred.

Suitable acids for conversion of the CN group in the compounds of the general formula (IV) into the amide group are, for example, hydrochloric acid, hydrochloric acid/water, BF3/acetic acid, hydrochloric acid/formic acid or hydrogen peroxide/sodium hydroxide solution/ethanol/water. Hydrochloric acid is preferred.

The pure enantiomers of the compounds of the general formula (I) according to the invention can be prepared, for example, by separating the corresponding unsubstituted enantiomerically pure acids by a customary method and then reacting them further as shown above.

The acids of the general formula (II) are known per se (M=H) or can be prepared by a customary method [cf. German Offenlecjungsschrift 3,818,443]. If M does not denote hydrogen, the compounds, as actual substance representatives, are new in some cases and can be prepared from the corresponding esters by hydrolysis according to a customary method.

The amines of the general formula (III) are likewise known or can be prepared according to customary methods.

The compounds of the general formula (IV) having the abovementioned meaning of Ri are new and can be prepared by alkylating cyano compounds of the general formula (V)

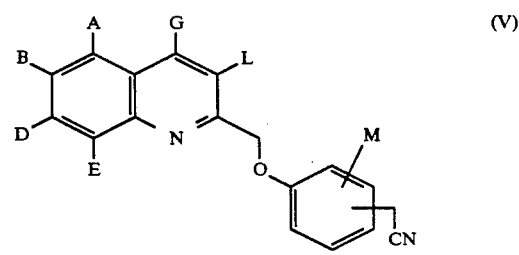

in which
A, B, D, E, G, L and M have the abovementioned meaning, with compounds of the general formula (VI)

$$R^1—Z \qquad (VI)$$

in which
$R^1$ has the abovementioned meaning and
Z represents halogen, preferably chlorine or bromine, in one of the abovementioned solvents, preferably dimethylformamide, in the presence of a base, preferably sodium hydroxide.

As intermediates, the compounds of the formula (V) are in some cases known from PCT WO 87/05510.

The compounds of the general formula (VI) are also known or can be prepared by a customary method (cf., for example, Beilstein 5, 19).

The compounds according to the invention can be employed as active substances in medicaments. The substances can act as inhibitors of enzymatic reactions in the context of arachidonic acid metabolism, in particular of 5-lipoxygenase.

The compounds of the general formula (I) surprisingly show a high in vitro activity as leukotriene synthesis inhibitors and a potent in vivo action after oral administration.

They are thus preferably suitable for the treatment and prevention of inflammations, in particular of diseases of the respiratory passages such as allergies-/asthma, bronchitis, emphysema, shock lung, pulmonary hypertension, inflammations/rheumatismandoedemas, thromboses and thromboembolisms, ischaemias (peripheral, cardiac, cerebral circulatory disorders), cardiac and cerebral infarcts, cardiac arrhythmias, angina pectoris, arteriosclerosis, in tissue transplantation, dermatoses such as psoriasis, inflammatory dermatoses, for example eczema, dermatophyte infection, infections of the skin by bacteria, metastases and for cytoprotection in the gastrointestinal tract.

The compounds according to the invention can be used both in human medicine and in veterinary medicine.

The pharmacological activity data of the substances according to the invention are determined by the following method:

As a measure of the 5-lipoxygenase inhibition in vitro, the release of leukotriene $B_4$ ($LTB_4$) in polymorphonuclear human leukocytes (PMN) was determined after addition of substances and Ca ionophore by means of reverse phase HPLC according to Borgeat, P. et al., Proc. Nat. Acad. Sci. 76, 2148–2152 (1979).

The present invention also includes pharmaceutical preparations which, in addition to inert, non-toxic, pharmaceutically suitable auxiliaries and excipients, contain one or more compounds of the general formula (I), or which consist of one or more active substances of the formula (I), and to processes for the production of these preparations.

The active substances of the formula (I) should be present in these preparations in a concentration of 0.1 to 99.5% by weight, preferably of 0.5 to 95% by weight, of the total mixture.

In addition to the active substances of the formula (I), the pharmaceutical preparations can also contain other pharmaceutical active substances.

The abovementioned pharmaceutical preparations can be prepared in a customary manner according to known methods, for example with the auxiliarylies) or excipient(s).

In general, it has proven advantageous to administer the active substance(s) of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, it may be advantageous to depart from the amounts mentioned, in particular depending on the type and on the body weight of the subject treated, on individual behaviour towards the medicoment, the nature and severity of the disease, the type of preparation and administration, and the time or interval at which administration takes place.

STARTING COMPOUNDS

Example I 4-(Quinolin-2-yl-methoxy)phenyl-acetonitrile

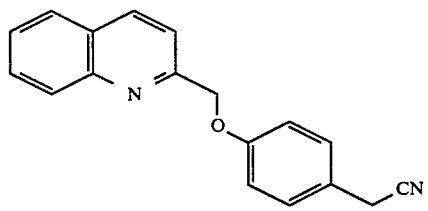

18 g (0.101 mol) of quinolin-2-yl-methyl chloride, 13.3 9 (0.1 mol) of 4-hydroxyphenylacetonitrile and 14 g (0.1 mol) of potassium carbonate (powdered and dried at 110° C.) are heated to boiling for 72 hours in 400 ml of dry acetone. The mixture is then allowed to cool, solid product is filtered off and the filtrate is evaporated to dryness in vacuo. The residue is taken up in 250 ml of dichloromethane, and the mixture is washed twice with 250 ml of 2N sodium hydroxide solution and then with water until neutral, dried using sodium sulphate and evaporated to dryness in vacuo. Recrystallisation takes place from diisopropyl ether/ethyl acetate.

Yield: 21.6 g (78.8% of theory)
m.p.: 104°–105° C. (colourless crystals)

Example II

2-[4-(Quinolin-2-yl-methoxy)phenyl]-2-cyclopentyl-acetonitrile

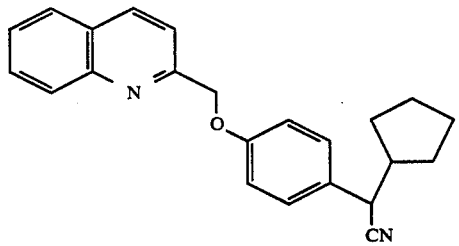

0.6 g of (80% strength) sodium hydride (0.02 mol) is suspended in 40 ml of abs. DMF and 5.5 g (0.02 mol) of the compound from Example I in 20 ml of DMF are added dropwise. Evolution of hydrogen commences. In the course of this, the temperature rises to room temperature. The mixture is stirred at room temperature for a further hour, then cooled to 0° C. and 3 g (0.02 mol) of cyclopentyl bromide are added dropwise. The mixture is additionally allowed to react overnight and then concentrated to dryness in vacuo, and the residue is stirred with 180 ml of water/dichloromethane (1:1). The organic phase is separated off, dried, concentrated to a small volume and separated by column chromatography (silica gel 60, eluent: toluene/ethyl acetate=9:1).
$R_f$=0.5
Yield: 4 g (53% of theory)
m.p.: 87° C. (colourless crystals)

Example III

Methyl 2-[3-isobutyl-4-(quinolin-2-yl-methoxy)-phenyl]-2-cyclohexyl-acetate

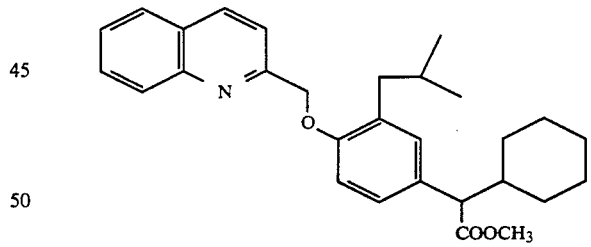

Under an argon atmosphere, 12 g (0.033 mol) of methyl 2-[3-isobutyl-4-(quinolin-2-yl-methoxy)phenylacetate and 6.52 g (0.04 mol)=4.0 ml of cyclohexyl bromide are dissolved in 36 ml of DMF and cooled to 0° C. 4.88 g (0.04 ml)- of potassium tertiary butoxide, dissolved in 80 ml of DMF, are added dropwise with stirring to this mixture. After a reaction time of about 2 h, the temperature is allowed to rise to room temperature, and the mixture is acidified with 2N hydrochloric acid and concentrated to dryness in vacuo. The residue which remains is stirred with 100 ml of dichloromethane and 50 ml of water, the organic phase is separated off, dried with $Na_2SO_4$ and concentrated to a small volume in vacuo, and the residue which remains is separated by column chromatography (silica gel 60, eluent:

dichloromethane/ethyl acetate=100:2). Slightly yellowish oil, yield:13 g (88.4% of theory)

Example IV

2-[3-Isobutyl-4-quinolin-2-yl-methoxy)phenyl]-2-cyclohexyl-acetic acid

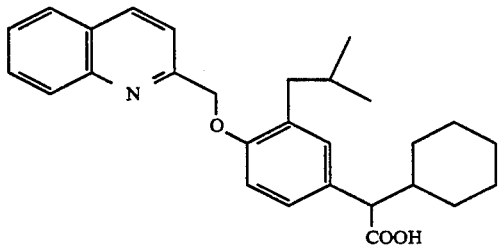

10.2 g (0.0236 mol) of the compound from Example III are taken up in 70 ml of 2-propanol and heated to boiling overnight with 50 ml of 1N sodium hydroxide solution. After cooling, the mixture is neutralised with 50 ml of 1N hydrochloric acid. The colourless precipitate obtained is filtered off with suction, washed and dried and then recrystallised from diisopropyl ether.

Colourless crystals: m.p. 130° C.

Yield: 9.5 g (96.3% of theory)

Examples V and VI (+)-2-[3-Isobutyl-4-(quinolin-2-yl-methoxy)phenyl]-2-cyclohexyl-acetic acid (V)

(−)-2-[3-Isobutyl-4-(quinolin-2-yl-methoxy)phenyl]-2-cyclohexyl-acetic acid (VI)

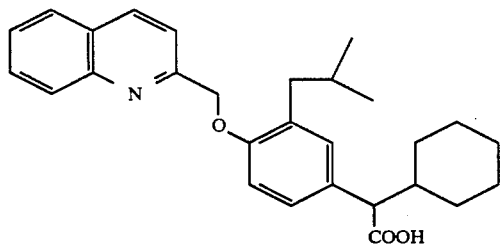

The title compounds are obtained by separation of the racemate (Example IV) by chromatographic separation on chiral columns

| (+)-Enantiomer: | spec. rotation: | 17.96 | CHCl₃ | (V) |
|---|---|---|---|---|
| | mol. rotation: | 77.41 | | |
| (−)-Enantiomer: | spec. rotation: | −18.86 | CHCl₃ | (VI) |
| | mol. rotation: | −81,28 | | |

Example VII

Methyl 2-[3-isobutyl-4-(quinolin-2-yl-methoxy)-phenyl]-2-cycloheptyl-acetate

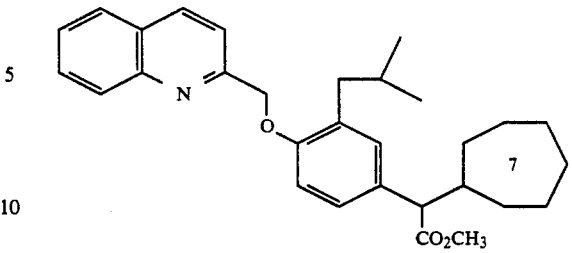

10 g (0.0275 mol) of methyl 2-[3-isobutyl-4-(quinolin-2-yl-methoxy)-phenylacetate are reacted with 10.04 g (0.055 mol) of cycloheptyl bromide and 6.17 g (0.055 mol) of potassium tertiary butoxide to give the title compound in analogy to the procedure of Example III.

Example VIII

2-[3-Isobutyl-4-(quinolin-2-yl-methoxy)phenyl]-2-cycloheptyl-acetic acid

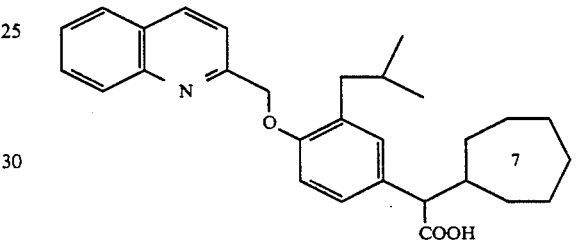

In analogy to the procedure of Example IV, the title compound is prepared from the above compound in 50 ml of 1N sodium hydroxide solution with subsequent acidification.

Colourless crystals: m.p.: 112° C.

Yield: 11.3 g

Examples IX and X (+)-2-[3-Isobutyl-4-(quinolin-2-yl-methoxy)phenyl]-2-cycloheptyl-acetic acid (IX)

(−)-2-[3-Isobutyl-4-(quinolin-2-yl-methoxy)phenyl]-2-cycloheptyl-acetic acid (X)

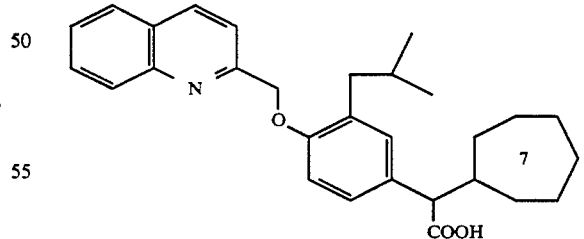

| (+)-Enantiomer: | spec. rotation: | 15.72, | solvent CHCl₃, |
|---|---|---|---|
| | mol. rotation: | 69.96 | (Example IX) |
| (−)-Enantiomer: | spec. rotation: | −18.7, | solvent CHCl₃, |
| | mol. rotation: | −86.19 | (Example X) |

The title compounds are obtained from the racemate (Example VIII) by chromatographic separation on chiral columns.

Example XI

Methyl 2-[3-isobutyl-4-(quinolin-2-cyclopentyl-acetate

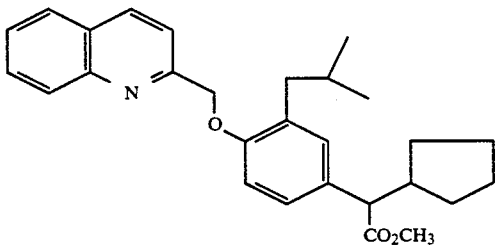

In analogy to the procedures of Examples III and VII, the title compound is prepared from 10 g (0.0275mol) of methyl 2-[3-isobutyl-4-(quinolin-2-yl-methoxy)phenylacetamide, 8.2 g (0.55 mol) of cyclopentyl bromide and 6.17 g (0.055 mol) of potassium tertiary butoxide. Yellow-brown oil Yield:quantitative

Example XII

2-[3-Isobutyl-4-(quinolin-2-yl-methoxy)phenyl]-2-cyclopentyl-acetic acid

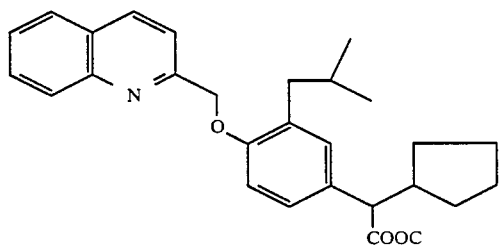

In analogy to the procedures of Examples IV and VIII, the title compound is prepared from the compound of Example XI by hydrolysis with 30 ml of sodium hydroxide solution and subsequent acidification.

Slightly yellowish crystals, m.p.: 120° C.
Yield:10.5 g (91.5% of theory)

Examples XIII and XIV (+)-2-[3-Isobutyl-4-(quinolin-2-yl-methoxy)phenyl]-2-cyclopentyl-acetic acid (XIII)
(−)-2-[3-isobutyl-4-(quinolin-2-yl-methoxy)phenyl]-2-cyclopentyl-acetic acid (XIV)

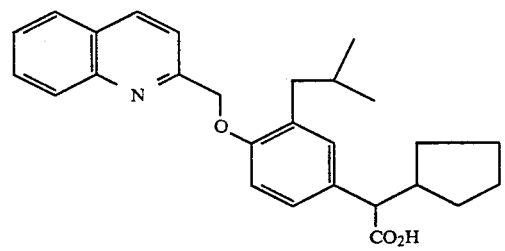

The title compounds are prepared by chromatographic separation of the compound of Example XII on chiral columns.

| (+)-Enantiomer: | spec. rotation: | 44.56, | (THF) |
|---|---|---|---|
| | mol. rotation: | 185.84 | (Example XIII) |
| (−)-Enantiomer: | spec. rotation: | −41.07, | (THF) |
| | mol. rotation: | −171.28 | (Example XIV) |

PREPARATION EXAMPLES

Example 1

2-[4-(Quinolin-2-yl-methoxy)phenyl]-2-cyclopentylacetamide

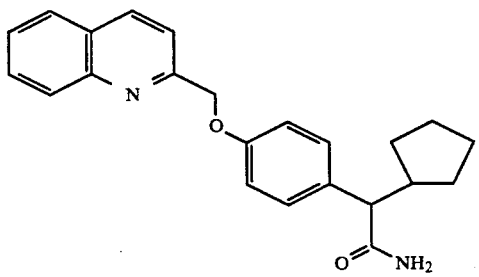

2 g (5.8 mmol) of the compound from Example II were suspended in 6 ml of conc. hydrochloric acid and stirred overnight at 40° C. After cooling to room temperature, THF is added until solution is complete and the mixture is neutralised with sodium hydrogen carbonate solution. The organic phase is separated off, dried with sodium sulphate and concentrated to a small volume in vacuo. Separation is carried out by column chromatography (silica gel 60, eluent: dichloromethane/ethyl acetate/glacial acetic acid (80:15:15).

$R_f$=0.35 (the acid is at $R_f$ about 0.68)
Yield:1.28 g (71.3% of theory)
m.p.:178° C. (colourless crystals)

Examples 2 and 3

(+)-2-[4-(Quinolin-2-yl-methoxy)phenyl]-2-cyclopentylacetamide (2)
(−)-2-[4-(Quinolin-2-yl-methoxy)phenyl]-2-cyclopentylacetamide (3)

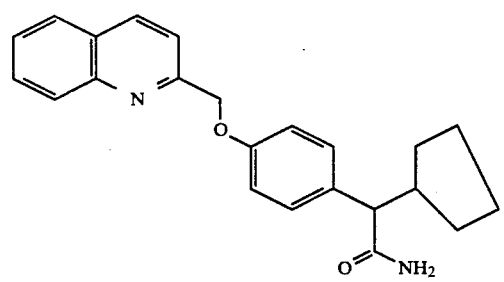

Examples (2) and (3) are prepared from the enantiomerically pure acids in analogy to the procedure of Example 1.

$[\alpha]_D$= +30.5 (THF) Example (2)
$[\alpha]_D$= −40.2 (THF) Example (3).

EXAMPLE 4

2-[4-(Quinolin-2-yl-methoxy)phenyl]-2-cycloheptylacetamide

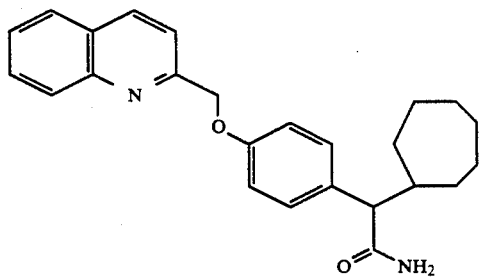

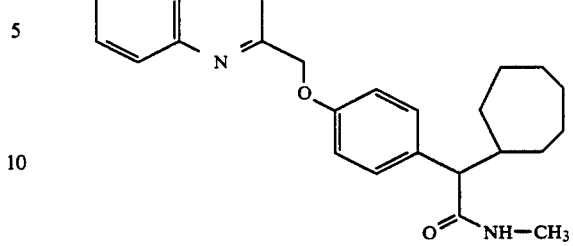

10 g (0.0257 mol) of 2-[4-(quinolin-2-yl-methoxy)-phenyl]-2-cycloheptyl-acetic acid are suspended under argon in 100 ml of dried dichloromethane, treated dropwise with 8.3 g (5.1 ml) (0.07 mol) of thionyl chloride (freshly distilled) and the mixture is heated under reflux for 2 hours. It is then concentrated to a small volume in vacuo, taken up rapidly in 20 ml of dried dichloromethane and cooled to −20° C., and a stream of dry ammonia is passed through the solution until it is saturated. A colourless precipitate is obtained. The mixture is additionally stirred at room temperature overnight, the suspension is stirred with water and filtered, and the filter cake is washed with water and recrystallised from THF.

Yield: 9.7 g (97% of theory)

m.p.: 178° C. (colourless crystals)

Examples 5 and 6

(+)-2-[4-(Quinolin-2-yl-methoxy)phenyl]-2-cycloheptylacetamide (5)

(−)-2-[4-(Quinolin-2-yl-methoxy)phenyl]-2-cycloheptylacetamide (6)

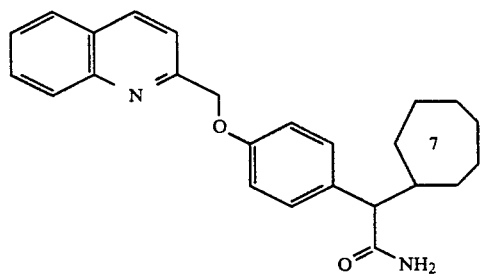

The compounds (5) and (6) are prepared from the enantiomerically pure acids in analogy to the procedure of Example 4.

$[\alpha]_D = +23.5$ (THF) Example (5)

$[\alpha]_D = -21.9$ (THF) Example (6).

Example 7

N-Methyl-2-[4-(quinolin-2-yl-methoxy)phenyl]-2-cycloheptyl-acetamide 6 g of 2-[4-(quinolin-2-yl-methoxy)phenyl]-2-cycloheptylacetic acid (0.015 mol) and 2.67 g (0.0165 mol) of carbonyldiimidazole are dissolved in 60 ml of THF. A dried (NaOH pellets) stream of methylamine is passed into this solution at 40° C. It is then concentrated to dryness in vacuo, the residue is stirred with 50 ml of water and 50 ml of toluene, the organic phase is separated off, dried with sodium sulphate and concentrated to a small volume, and the mixture is separated by column chromatography (silica gel 60, eluent: toluene-/ethyl acetate/glacial acetic acid=7:2:1). The sample isolated is recrystallised from diisopropyl ether.

Yield: 3.66 g (58.8% of theory)

m.p.: 131° C. (colourless crystals)

Example 8

N-Cyclopentyl-2-[4-(quinolin-2-yl-methoxy)phenyl]-2-cycloheptyl-acetamide

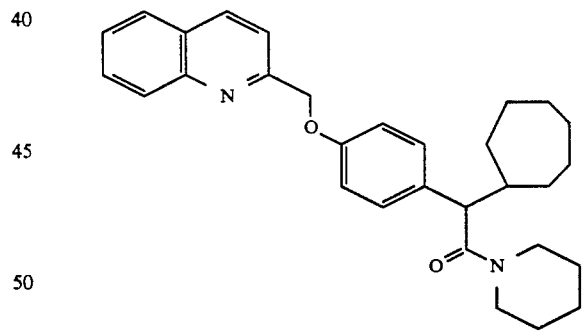

Analogously to Example 7, the title compound is obtained from 6 g (0.015 mol) of 2-[4-(quinolin-2-yl-methoxy)phenyl]-2-cycloheptyl-acetic acid, 5.34 g (0.033 mol) of carbonyldiimidazole and 170 g (2 mol) of piperidine. Chromatographic separation is carried out using silica gel 60, eluent: dichloromethane/methanol=100:5.

Yield: 0.8 g (11.7% of theory)

m.p.: 125° C. (colourless crystals)

The compounds listed in Tables 1, 2 and 3 can be prepared in analogy to the preparation procedures listed above:

TABLE 1
| Ex. No. | R¹ | R² | R³ | Yield (% of theory) | M.p. (°C.) |
|---|---|---|---|---|---|
| 9 | cyclopentyl | —C₂H₅ | —C₂H₅ | | |
| 10 | cyclopentyl | cyclohexyl | H | | |
| 11 | cyclopentyl-CH₂— | —CH₂— | H | 75 | 138 |
| 12 | cyclopentyl | —CH₂— | H | 73 | 137 |
| 13 | cyclopentyl | —C₂H₅ | H | 63 | 145 |
| 14 | cyclohexyl | —C₂H₅ | H | 75 | 144 |
TABLE 2
| Ex. No. | R¹ | X | Salt | Enantiomer |
|---|---|---|---|---|
| 15 | cycloheptyl | —N(piperazinyl)—C₆H₄—CF₃ | | |
| 16 | cycloheptyl | —N(piperazinyl)—CH₂—CH=CH—C₆H₅ | | |
| 17 | cycloheptyl | —N(piperazinyl)—(CH₂)₂—C₆H₅ | HCl | |

TABLE 2-continued

| Ex. No. | R¹ | X | Salt | Enantiomer |
|---|---|---|---|---|
| 18 | cycloheptyl-CH₃ | $-N\underset{\smile}{\frown}N-CH_2-CH=CH-C_6H_5$ | | (+) |
| 19 | cycloheptyl-CH₃ | $-N\underset{\smile}{\frown}N-CH_2-CH=CH-C_6H_5$ | | (−) |

TABLE 3

| Ex. No. | D | R¹ | X |
|---|---|---|---|
| 20 | Cl | cyclopentyl-CH₃ | $-N\underset{\smile}{\frown}N-CH_2-CH=CH-C_6H_5$ |

Example 21

2-[3-Isobutyl-4-(quinolin-2-yl-methoxy)-phenyl]-2-cyclohexylacetamide 1.8 g (0.004 mol) of 2-[3-isobutyl-4-(quinolin-2-ylmethoxy)-phenyl]-2-cyclohexylacetic acid and 9.65 g (0.004 mol) of N,N'-carbonyl-diimidazole are dissolved in 30 ml of abs. THF and stirred overnight at 50° C. The mixture is evaporated to dryness in vacuo, taken up in 50 ml of ethyl acetate and extracted twice by shaking with 50 ml of water. The organic phase is separated off, dried using Na₂SO₄ and concentrated to dryness in vacuo. Recrystallisation takes place in diisopropyl ether. Yield:1.45 g (76.3% of theory) of colourless crystals.

1.55 g (0.003 mol) of the imidazolide prepared in this way are dissolved in 20 ml of absolute THF, the solution is treated with a spatula tipful of ammonium chloride and a stream of dry ammonia is passed in at 50° C. (about 5 h). The saturated mixture is allowed to stand overnight. A colourless precipitate is obtained. Everything is evaporated to dryness and the residue is recrystallised from diisopropyl ether.

Yield:0.7 g (54.3% of theory) of colourless crystals; m.p.:193°–5° C.

Example 22

N,N-Dimethyl-2-[3-isobutyl-4-(quinolin-2-yl-methoxy)phenyl]-2-cycloheptylacetamide

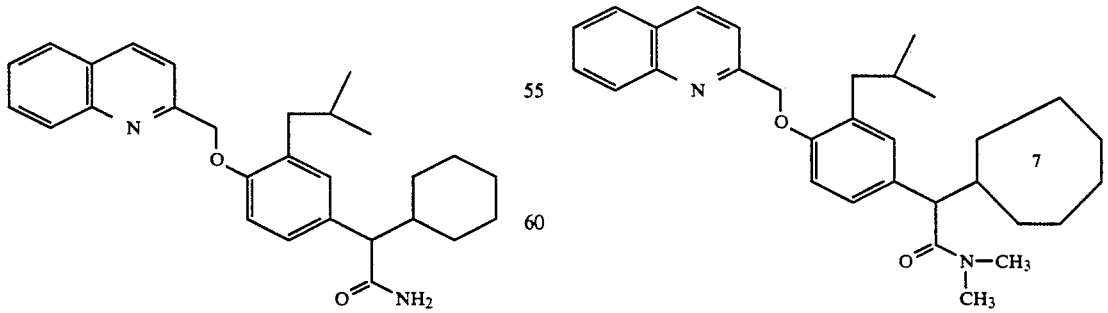

The title compound is prepared from 4.0 g (0.0091 mol) of 2-[3-isobutyl-4-(quinolin-2-yl-methoxy)phenyl]-2-cycloheptylacetic acid (Example VIII), 1.8 g (0.0111 mol) of N,N'-carbonyldiimidazole and dimethylamine gas in analogy to the procedure of Example 21. The reaction mixture is separated by column chromatography (silica gel 60, toluene/ethyl acetate/glacial acetic acid=8:1:1; $R_f$=0.4).

Yield:0.8 g (21% of theory) of colourless crystals; m.p.:114° C.

Example 23

2-[3-Isobutyl-4-(quinolin-2-yl-methoxy)phenyl]-2-cycloheptylacetamide

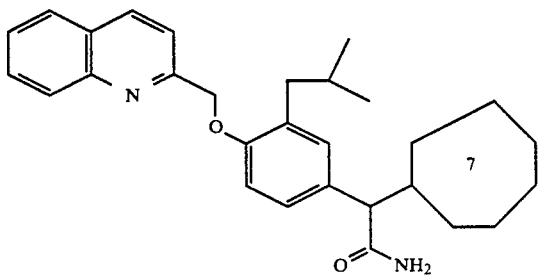

The title compound is prepared from 4.6 g (0.0104 mol) of 2-[3-isobutyl-4-(quinolin-2-yl-methoxy)phenyl]-2-cycloheptylacetic acid (Example VIII), 2.2 g (0.013 mol) of N,N'-carbonyldiimidazole and ammonia in analogy to the procedure of Example 21. Recrystallisation takes place from toluene; colourless crystals, m.p.: 193° C.

Yield:2.9 g (63% of theory).

Example 24

N-Methyl-2-[3-isobutyl-4-(quinolin-2-yl-methoxy)-phenyl]-2-cycloheptylacetamide

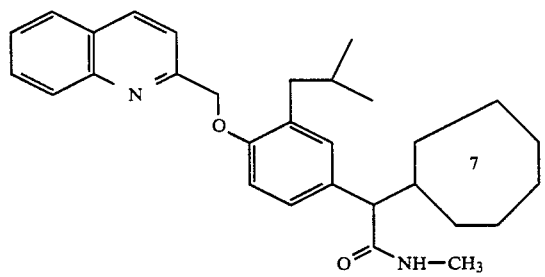

In analogy to the procedure of Example 21, the title compound is prepared from 3.0 g (0.00674 mol) of 2-(3-isobutyl-4-(quinolin-2-yl-methoxy)phenyll-2-cycloheptylacetic acid, 1.4 g (0.0082 mol) of N,N'-carbonyl-diimidazole and methylamine gas (50°-60° C., 5 h). Recrystallisation takes place from diisopropyl ether; colourless crystals, m.p.: 141° C.

Yield:2.5 g (81% of theory).

We claim:

1. Quinolylmethoxyphenyl-acetamide of the formula

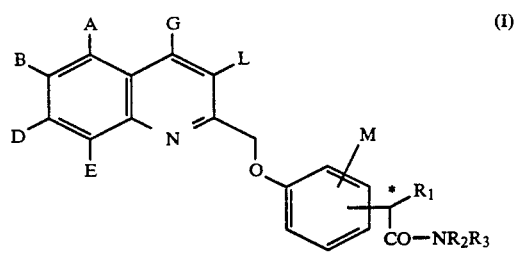

in which
A, B, D, E, G, L and M independently of one another represent hydrogen, hydroxyl, halogen, cyano, carboxyl, nitro, trifluoromethyl, trifluoromethoxy or represent straight-chain or branched alkyl or alkoxy each having up to 8 carbon atoms, or represent aryl having 6 to 10 carbon atoms, which is optionally substituted by halogen, hydroxyl, nitro or cyano, $R^1$ represents cycloalkyl having 3 to 12 carbon atoms, which is optionally substituted by straight-chain or branched alkyl having up to 8 carbon atoms, $R^2$ and $R^3$ are identical or different and represent hydrogen or straight-chain or branched alkyl having up to 8 carbon atoms, or represent benzyl, or represent cycloalkyl having 3 to 12 carbon atoms, which is optionally substituted by straight-chain or branched alkyl having up to 8 carbon atoms, or $R^2$ and $R^3$, together with the nitrogen atom, form a heterocyclic ring of the formula

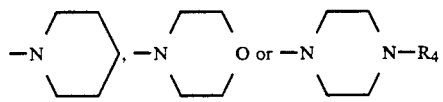

in which
$R^4$ denotes straight-chain or branched alkyl or alkenyl each having up to 8 carbon atoms, each of which is optionally substituted by phenyl or denotes phenyl which is optionally substituted by halogen or trifluoromethyl,
optionally in an isomeric form, or a salt thereof.

2. Quinolylmethoxyphenyl-acetamide according to claim 1,
in which
A, B, D, E, G, L and X independently of one another represent hydrogen, hydroxyl, fluorine, chlorine, bromine, carboxyl, nitro, trifluoromethyl, trifluoromethoxy or represent straight-chain or branched alkyl or alkoxy each having up to 6 carbon atoms, or represent phenyl which is optionally substituted by fluorine, chlorine, bromine, hydroxyl, nitro or cyano, $R^1$ represents cyclopropyl, cyclobutyl, cyclopentyl, cyclohexyl, cycloheptyl or cyclooctyl, each of which is optionally substituted by straight-chain or branched alkyl having up to 6 carbon atoms, $R^2$ and $R^3$ are identical or different and represent hydrogen or straight-chain or branched alkyl having up to 6 carbon atoms, or represent benzyl, or represent cyclopropyl, cyclobutyl, cyclopentyl, cyclohexyl, cycloheptyl or cyclooctyl, each of which is optionally substituted by straight-chain or branched alkyl having up to 6 carbon atoms, or R² and R³, together with the nitrogen atom, form a heterocyclic ring of the formula

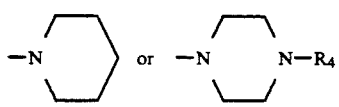

in which
R⁴ denotes straight-chain or branched alkyl or alkenyl each having up to 6 carbon atoms, each of which is optionally substituted by phenyl or denotes phenyl which is optionally substituted by fluorine, chlorine or trifluoromethyl,
if appropriate in an isomeric form, or a salt thereof.

3. Quinolylmethoxyphenyl-acetamide according to claim 1,
in which
A, B, D, E, G, L and M independently of one another represent hydrogen, hydroxyl, fluorine, chlorine, bromine or straight-chain or branched alkyl having up to 4 carbon atoms,
R¹ represents cyclopropyl, cyclopentyl, cyclohexyl or cycloheptyl, each of which is optionally substituted by straight-chain or branched alkyl having up to 4 carbon atoms,
R² and R³ are identical or different and represent hydrogen or straight-chain or branched alkyl having up to 4 carbon atoms, or represent benzyl, or represent cyclopropyl, cyclopentyl, cyclohexyl or cycloheptyl, each of which is optionally substituted by straight-chain or branched alkyl having up to 4 carbon atoms, or
R² and R³, together with the nitrogen atom, form a heterocyclic ring of the formula

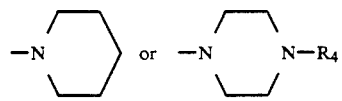

in which
R⁴ denotes straight-chain or branched alkyl or alkenyl each having up to 4 carbon atoms, each of which is optionally substituted by phenyl or denotes phenyl which is optionally substituted by fluorine, chlorine or trifluoromethyl,
optionally in an isomeric form, or a salt thereof.

4. A compound according to claim 1 wherein such compound is 2-[4-(quinolin-2-yl-methoxy)phenyl]-2-cyclopentyl-acetamide of the formula

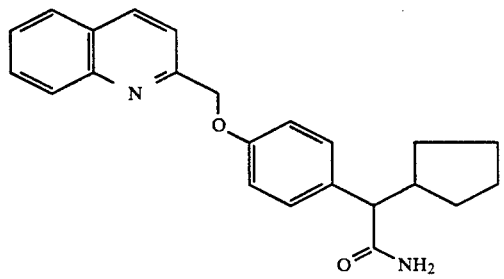

its enantiomers or a salt thereof.

5. A compound according to claim 1 wherein such compound is 2-[4-(quinolin-2-yl-methoxy)phenyl]-2-cycloheptyl-acetamide of the formula

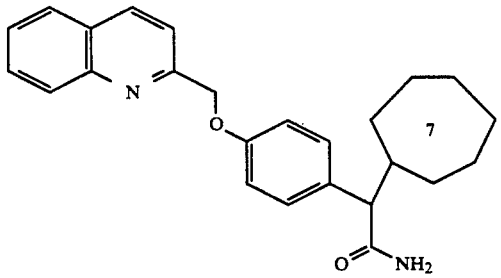

its enantiomers or a salt thereof.

6. A compound according to claim 1 wherein such compound is N-Methyl-2-[4-(quinolin-2-yl-methoxy)-phenyl]-2-cycloheptyl-acetamide of the formula

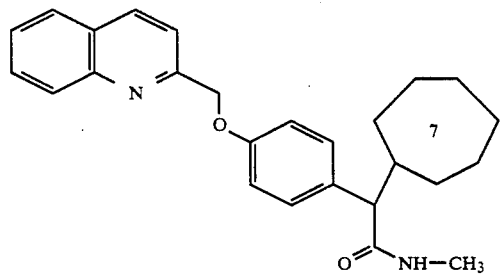

or their salts.

7. A compound according to claim 1 wherein such compound is N-cyclopentyl-2-[4-(quinolin-2-yl-methoxy)phenyl]-2-cycloheptylacetamide of the formula

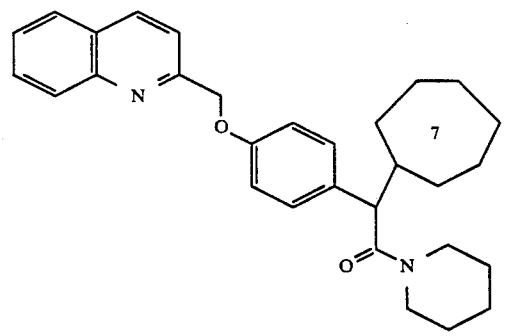

or a salt thereof.

8. A compound according to claim 1 wherein such compound is 2-[3-isobutyl-4-(quinolin-2-yl-methoxy)-phenyl]-2-cyclohexyl-acetamide of the formula

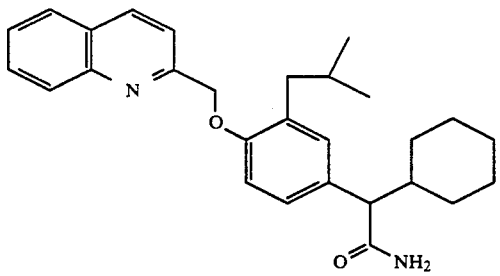

or a salt thereof.

9. A compound according to claim 1 wherein such compounds is 2-[3-isobutyl-4-(quinolin-2-yl-methoxy)-phenyl9 -2-cycloheptyl-acetamide of the formula

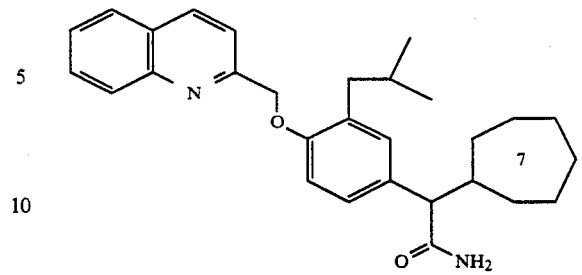

or a salt thereof.

10. A composition for the inhibition of enzymatic reactions in the context of arachidonic acid metabolism comprising an amount effective therefor of a compound or salt thereof according to claim 1 and a pharmacologically acceptable diluent.

11. The method of inhibiting enzymatic reactions in the context of arachidonic acid metabolism in a patient in need thereof which comprises administering to such patient an amount effective therefor of a compound or salt thereof according to claim 1.

* * * * *

UNITED STATES PATENT AND TRADEMARK OFFICE
CERTIFICATE OF CORRECTION

PATENT NO. : 5,310,744

DATED : May 10, 1994

INVENTOR(S) : Siegfried Raddatz, et al.

It is certified that error appears in the above-identified patent and that said Letters Patent are hereby corrected as shown below:

| | |
|---|---|
| Col.20, Line 50 | Delete "X" and substitute --M-- |
| Col. 23, Line 23 | Delete "compounds" and substitute --compound-- |
| Col. 23, Line 25 | Delete "9" and substitute --]-- |

Signed and Sealed this

Twenty-first Day of September, 1999

Attest:

Q. TODD DICKINSON

*Attesting Officer*     *Acting Commissioner of Patents and Trademarks*